United States Patent [19]

Coleman et al.

[11] 4,434,096

[45] Feb. 28, 1984

[54] SUBSTRATES FOR THE QUANTITATIVE DETERMINATION OF PROTEOLYTIC ENZYMES

[75] Inventors: Patrick L. Coleman, Ypsilanti, Mich.; John A. Wehrly, Wilmington, Del.

[73] Assignee: E. I. Du Pont de Nemours and Company, Wilmington, Del.

[21] Appl. No.: 279,161

[22] Filed: Jun. 30, 1981

[51] Int. Cl.$^3$ ............................................ C07C 103/52
[52] U.S. Cl. ............................................ 260/112.5 R
[58] Field of Search .................. 260/112.5 R; 424/177

[56] References Cited

U.S. PATENT DOCUMENTS

| | | | |
|---|---|---|---|
| 3,119,668 | 1/1964 | Ellman | 23/230 |
| 3,867,364 | 2/1975 | Umezaea et al. | 424/177 |
| 3,884,896 | 5/1975 | Blomback et al. | 260/112.5 R |
| 4,016,042 | 4/1977 | Svendsen | 195/103.5 R |
| 4,061,625 | 12/1977 | Ekenstam et al. | 260/112.5 R |
| 4,070,245 | 1/1978 | Svendsen | 195/99 |
| 4,137,225 | 1/1979 | Ekenstam | 260/112.5 R |
| 4,166,825 | 1/1979 | Plattner et al. | 260/455 |

FOREIGN PATENT DOCUMENTS 2034326 6/1980 United Kingdom .
2034325 6/1980 United Kingdom .

OTHER PUBLICATIONS

Goldenberg et al., J.A.C.S., 72, 5317, (1950).
Farmer et al., J. of Biological Chemistry, 250, 7366 (1975).
Green et al., Analytical Biochemistry, 93,223, (1979).
Castillo et al., Analytical Biochemistry, 99, 53 (1979).
Brian J. McRae, "Thesis", Georgia Inst. of Tech., Dec. 1980.
McRae et al., Biochemistry, 20, 7196–7206, (1981).
Chemical Abstracts, vol. 87, 1977, p. 211, abstract No. 179595u, Korsan-Bengtsen et al., "Determination of Plasma Prothrombin With the Chromogenic Peptide Substrate H-D-Phe-Pip-Arg-p NA".
Christensen et al., Biochimica et Biophysica Acta, 569 (1979), 177–183.

Primary Examiner—Delbert R. Phillips
Assistant Examiner—F. T. Moezie

[57] ABSTRACT

There is provided a group of tripeptide thiol ester substrates of the following generalized structure:

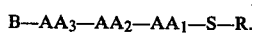

$$B-AA_3-AA_2-AA_1-S-R.$$

These substrates yield, upon enzymatic cleavage of the thiol ester bond, thiols which can be quantified accurately through certain coupling reactions. The substrates are useful for the quantitative determination of proteolytic enzymes in biological fluids.

4 Claims, No Drawings

SUBSTRATES FOR THE QUANTITATIVE DETERMINATION OF PROTEOLYTIC ENZYMES

DESCRIPTION

1. Technical Field

This invention relates to synthetic substrates for the quantitative determination of proteolytic enzymes and more particularly to tripeptide thiol ester substrates.

2. Background Art

Synthetic oligopeptide derivatives have been widely used as substrates in the assay of proteolytic enzymes such as thrombin, trypsin and plasmin. The peptide substrate is designed to mimic the relevant amino acid sequence of the natural substrate, usually a protein. This amino acid sequence determines the selectivity of a substrate for a given enzyme. (U.S. Pat. Nos. 3,884,896, 4,061,625, 4,070,245, and 4,137,225 disclose a variety of synthetic substrates for different proteolytic enzymes.) For such proteolytic enzymes, the carboxyl terminus amino acid of the substrate is preferentially lysine or arginine which, in turn, is coupled to an appropriate chromophore or fluorophore detector group. The enzyme cleaves the substrate at the carboxyl terminus, releasing the free chromophore which can be accurately measured photometrically or the free fluorophore which is measured fluorometrically. These substrates offer a rapid, sensitive and precise means to assay enzymes, proenzymes or inhibitors of clinical interest.

The most commonly used detector group with such substrates is p-nitroaniline which can be attached covalently at the carboxyl terminus through an amide bond. Upon enzymatic cleavage, p-nitroaniline is released and is measured by the absorbance at or near 405 nm where the molar absorptivity ($\epsilon^{405}$ nm) is approximately 10,500 1/mole-cm. Tripeptide and tetrapeptide sequences have been identified which make these substrates selective for enzymes such as thrombin, plasmin, kallikrein or factor $X_a$.

Thiol esters have been described as substrates for proteolytic enzymes; see, for example, Goldenberg, et al., J. Am. Chem. Soc., Volume 72, 5317 (1950), and recently have been applied to serine proteases, see, for example, Green, et al., Anal. Biochem., Volume 93, 223 (1979), Farmer, et al., J. Biol. Chem., Volume 250, 7366 (1975), and U.S. Pat. No. 4,166,825. These substrates have primarily been single amino acid derivatives and, in principle, function in a manner similar to the p-nitroaniline derivatives. A free thiol group is released during enzymatic attack and is measured photometrically through a coupling agent. Such coupling agents as 5,5'-dithiobis(2-nitrobenzoic acid) (DTNB) have been described in U.S. Pat. No. 3,119,668.

Tripeptide thiol ester substrates have not been used in enzymatic assays, although the prior art does include one reference to a tetrapeptide thiol ester as a substrate for the proteolytic enzyme elastase, Castillo, et al., Anal. Biochem., Volume 99, 53 (1979). Tetrapeptide thiol ester substrates, however, are not expected to have a sufficient compatibility for a broad group of enzymes.

DISCLOSURE OF THE INVENTION

The substrates of the present invention combine the selectivity of the tripeptide p-nitroaniline substrates with the sensitivity of the detector group inherent in the thiol ester substrates and consist essentially of compounds having the generalized formula:

$$B-AA_3-AA_2-AA_1-S-R$$

where
- B is acetyl, benzoyl, benzyloxycarbonyl, butoxycarbonyl, tosyl or H (when $AA_3$ is a D-configuration amino acid);
- $AA_3$ is Val, Pro, Gly, Phe, Ala, Ile, Leu, Glu or Pip;
- $AA_2$ is Leu, Pro, Ala, Phe, Val, Tyr, Thr or Pip
- $AA_1$ is Lys, Arg or Orn; and
- R is an alkyl group of 1-4 carbon atoms or benzyl; and
biologically compatible salts thereof.

DESCRIPTION OF THE INVENTION

The tripeptide thiol ester substrates of the general structure $B-AA_3-AA_2-AA_1-S-R$ and salts thereof are themselves not chromogenic substrates. Coupling of the detector group thiols through external agents, after enzymatic hydrolysis, is necessary for color development. Among such coupling agents in DTNB. Other compounds similar to DTNB can also be used, such as 2,2'-dithiodipyridine or 4,4'-dithiodipyridine. Although these coupling agents may afford higher sensitivity, they do not possess the desirable water solubility or stability of DTNB. DTNB has good sensitivity, $\epsilon^{412\ nm} = 14,150$ 1/mole-cm and is superior to the most commonly utilized synthetic substrate detector group, para-nitroaniline.

An additional advantage of these tripeptide thiol ester substrates is the potential for coupling the free thiol group released upon enzymatic cleavage to a fluorescent label such as dibromobimane or N-(iodoacetylaminoethyl)-5-naphthylamine-1-sulfonic acid. Such fluorescent adducts can further increase the sensitivity of these tripeptide thiol ester substrates.

Thiol ester substrates are superior to previously used carboxyl ester substrates (e.g., p-nitrophenyl esters of lysine, arginine or peptides) in their stability under physiological conditions as was described in the article by Green, et al., referred to above. Although not as stable under more alkaline conditions as the amide substrates, the thiol ester substrates of this invention possess superior sensitivity in the measurement of proteolytic enzymes when compared to the commonly used amide substrates.

The choice of a given substrate for a particular enzyme is guided primarily by the kinetic behavior of the substrate with that particular enzyme in comparison to other, potentially interfering enzymes present in the sample to be analyzed. The Michaelis-Menten constant, $K_m$, is a kinetic parameter related to the affinity of a substrate for an enzyme under a given set of reaction conditions. The $K_m$ is defined as the substrate concentration at which the initial reaction velocity is one-half of the maximal initial reaction velocity. The maximal velocity ($v_{max}$), another important kinetic parameter, when divided by the enzyme concentration, yields $k_{cat}$. The determination of $K_m$ and $k_{cat}$ for a given substrate with various enzymes allows the determination of the selectivity of that substrate for a given enzyme.

$K_m$ and $v_{max}$ values can be determined by utilizing a centrifugal analyzer (GEMSAEC system, available from Electro-Nucleonics, Inc., Fairfield, N.J.) to measure the initial rates of substrate hydrolysis by the proteolytic enzyme. Five substrate concentrations ([S]), ranging from about one-fifth to five times the expected $K_m$, can be used for triplicate determinations in this centrifugal analyzer. The initial reaction rates (v) can then be plotted in a Hanes plot, [S]/v versus [S], for a determination of $K_m$ (the absolute value of the X-intercept) and $v_{max}$ (the reciprocal of the slope) through linear regression analysis. Alternative procedures are available for the calculation of $K_m$ and $v_{max}$.

For a given enzyme, lower $K_m$ values for a series of substrates indicate higher affinity of the substrate to the enzyme. This allows the utilization of lesser amounts of substrate while still operating at $v_{max}$. The following values indicate this advantage of a tripeptide thiol ester substrate, over a known thiol ester, for human α-thrombin:

|  | $K_m$ (μm) | $k_{cat}$ (sec$^{-1}$) |
|---|---|---|
| H—D-Val—Leu—Lys—S—Bzl | 16 | 94 |
| Z—Lys—S—Bzl | 38 | 84 |

Standard amino acid abbreviations are used and are given below. Unless otherwise stated, all amino acids have the L-configuration. The tripeptide sequence is given with the amino terminus (free —NH₂ end or blocked with an appropriate group) at the left and the carboxyl group at the right:

| | |
|---|---|
| Ala = alanine | Orn = ornithine |
| Arg = arginine | Phe = phenylalanine |
| Glu = glutamic acid | Pip = pipecolic acid |
| Gly = glycine | Pro = proline |
| Ile = isoleucine | Thr = threonine |
| Leu = leucine | Tyr = tyrosine |
| Lys = lysine | Val = valine |

Additional abbreviations are Bzl=benzyl, Z=benzyloxycarbonyl, and Boc=tert-butyloxycarbonyl.

The choice of R will be determined by factors such as solubility of the substrate and of the thiol hydrolysis product, substrate selectivity, and convenience of synthesis. Benzyl group is most preferred, while methyl and ethyl are also preferred.

The substrates of this invention can be used diagnostically in the determination of proteolytic enzymes present in biological fluids, their inactive precursors (proenzymes) or proteolytic inhibitors. For example, the substrate H-D-Val-Leu-Lys-S-Bzl can be used in an assay for the proenzyme plasminogen. In this assay, sufficient streptokinase is added to plasminogen to form an enzymatically active complex. This complex cleaves the substrate, releasing benzyl mercaptan, which can be measured through a reaction with DTNB. The intensity of the yellow color is the measure of the plasminogen concentration.

EXAMPLE

Preparation of H-D-Leu-Pro-Arg-S-Bzl.2HCl

The preparation of this substrate follows the following scheme:

Step A

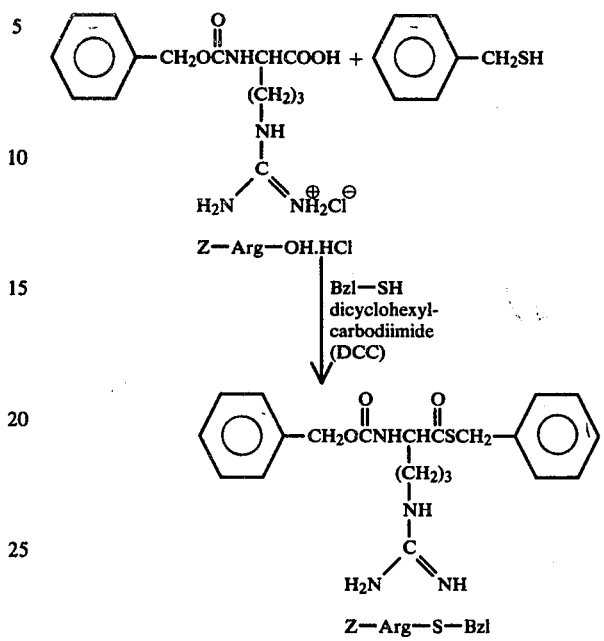

Step B

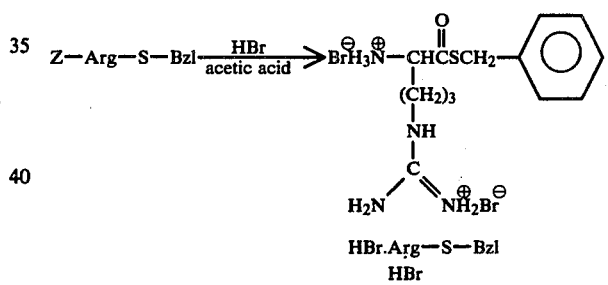

Step C

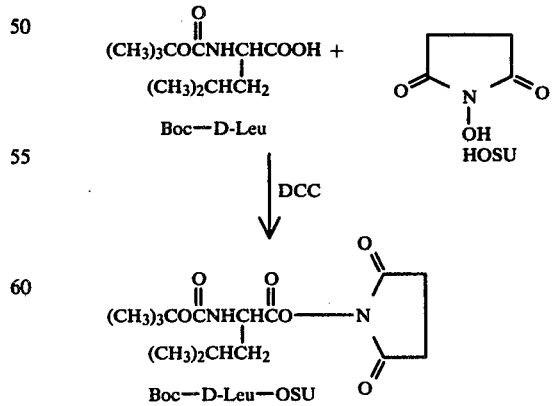

Step D

-continued

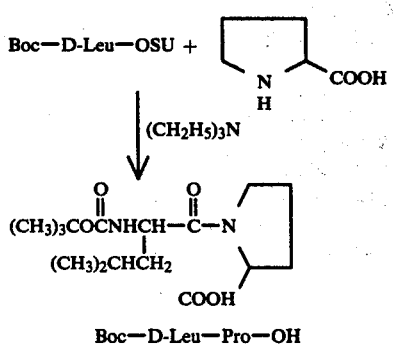

Step E

Boc—D-Leu—Pro—OH + HBr.Arg—S—Bzl
HBr

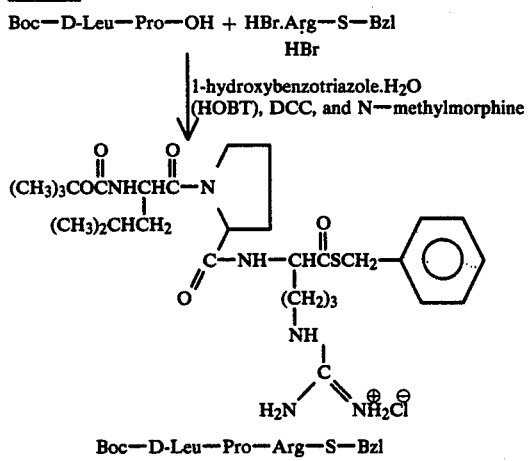

Boc—D-Leu—Pro—Arg—S—Bzl

Step F

Boc—D-Leu—Pro—Arg—S—Bzl + HCl

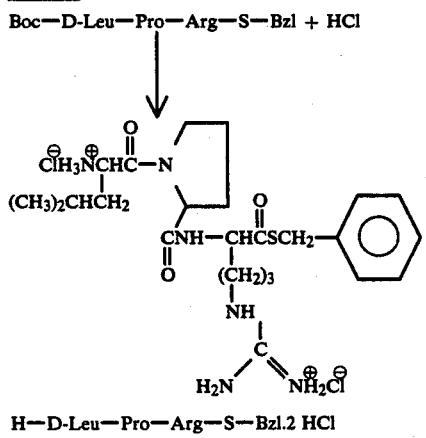

H—D-Leu—Pro—Arg—S—Bzl.2 HCl

Step A. Preparation of Z-Arg-S-Bzl

Z-Arg-OH.HCl (6 g, 8.7 mmoles) and benzyl mercaptan (4.2 ml, 17.4 mmoles) are dissolved in dimethylformamide (DMF) and cooled to 0° C. DCC (3.6 g, 8.7 mmoles), dissolved in DMF, is then added to the above reaction mixture, stirred at 0° C. for 30 minutes, then stirred overnight at room temperature. The precipitate formed is removed by filtration and the filtrate is concentrated under vacuum to yield an oil. This oily residue is dissolved in ethyl acetate and washed, successively, with 0.1 N HCl, 5% NaHCO$_3$, and saturated aqueous NaCl. The organic layer is dried over anhydrous Na$_2$SO$_4$ and the solvent removed by evaporation. The crude product is purified by silica gel column, using a CHCl$_3$/methanol system, yielding 4.5 g of the product.

Step B Preparation of

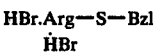

HBr.Arg—S—Bzl
HBr 2.1 g of Z-Arg-S-Bzl, prepared in Step A above, and saturated HBr are placed in a 100-ml round-bottomed flask and stirred at room temperature for 3 hours. The solvent is evaporated and the residue is crystallized from isopropyl alcohol and petroleum ether, yielding 1.9 g of pure product.

Step C Preparation of Boc-D-Leu-OSU

Boc-D-Leu (2.5 g, 10.03 mmoles) is dissolved in THF.HOSU (1.27 g, 11.03 mmoles) and DCC (2.29 g, 11.03 mmoles) are added and the mixture stirred at room temperature for 3–4 hours. The insoluble dicyclohexyl urea formed is filtered and the filtrate is concentrated to dryness. The residue is recrystallized from ethanol yielding 2.3 g of the product.

Step D Preparation of Boc-D-Leu-Pro-OH

Proline (0.842 g, 7.31 mmoles), in its HCl salt form, is dissolved in DMF and stirred with Boc-D-Leu-OSU (2.4 g, 7.31 mmoles) and (C$_2$H$_5$)$_3$N (1.02 ml, 7.31 mmoles), prepared in Step C above, at room temperature overnight. The reaction mixture is filtered and the filtrate is concentrated under vacuum to dryness. The residue is dissolved in ethyl acetate washed with 0.1 N HCl, and then washed twice with H$_2$O. The organic layer is dried over anhydrous Na$_2$SO$_4$ and the solvent removed by evaporation. The crude product is purified by silica gel column, yielding 1.4 g of pure Boc-D-Leu-Pro-OH.

Step E Preparation of Boc-D-Leu-Pro-Arg-S-Bzl 1.2 g (3.52 mmoles) of Boc-D-Leu-Pro-OH, prepared in Step D above, is dissolved in DMF and

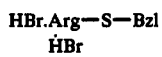

HBr.Arg—S—Bzl
HBr (1.9 g, 3.2 mmoles), prepared in Step B above, HOBT (0.48 g, 3.52 mmoles), and DCC (0.73 g, 3.52 mmoles) are added, followed by 1.30 g of N-methylmorphine, and the reaction mixture stirred at −10° C. for 30 minutes, then overnight at room temperature. The precipitate formed, containing dicyclohexyl urea, is filtered and the filtrate is concentrated under vacuum to yield an oil. This residue is dissolved in CHCl$_3$ and washed with 0.1 N HCl and saturated aqueous NaCl. The organic layer is dried over anhydrous Na$_2$SO$_4$ and the solvent removed by evaporation. A portion of the crude product is purified by silica gel column, using CHCl$_3$/methanol to elute the product, yielding 0.845 g of pure Boc-D-Leu-Pro-Arg-S-Bzl.HCl.

Step F Preparation of H-D-Leu-Pro-Arg-S-Bzl.2HCl

Boc-D-Leu-Pro-Arg-S-Bzl (0.845 g), prepared in Step E above, is mixed with HCl for approximately 30 minutes to remove the Boc protecting group. The product is precipitated with ether to give 0.713 g of pure H-D-Leu-Pro-Arg-S-Bzl.2HCl.

We claim:

1. Tripeptide thiol ester substrates consisting essentially of compounds having the structure:

H—AA$_3$—AA$_2$—AA$_1$—S—R wherein
AA$_3$ is a D-configuration amino acid; and where
AA$_3$ is selected from the group consisting of Val, Pro, Gly, Phe, Ala, Ile, Leu, Glu and Pip;
AA$_2$ is selected from the group consisting of Leu, Pro, Ala, Phe, Val, Tyr, Thr and Pip;
AA$_1$ is selected from the group consisting of Lys, Arg and Orn; and
R is an alkyl group of 1-4 carbon atoms or benzyl; and
biologically compatible salts thereof.

2. The substrate of claim 1 where AA$_3$ is Val, AA$_2$ is Leu, AA$_1$ is Lys, and R is benzyl.

3. The substrate of claim 1 where AA$_3$ is Phe, AA$_2$ is Pro, AA$_1$ is Arg, and R is benzyl.

4. The substrate of claim 1 where AA$_3$ is Leu, AA$_2$ is Pro, AA$_1$ is Arg, and R is benzyl.

* * * * *